United States Patent [19]

Brune

[11] Patent Number: 4,851,443

[45] Date of Patent: Jul. 25, 1989

[54] CARBOXYLIC ACID AMIDES, COMPOSITIONS AND MEDICAL USE THEREOF

[75] Inventor: Kay Brune, Marloffstein-Rathsberg, Fed. Rep. of Germany

[73] Assignee: Smith Kline Dauelsberg, GmbH, Göttingen, Fed. Rep. of Germany

[21] Appl. No.: 214,969

[22] Filed: Jul. 5, 1988

Related U.S. Application Data

[62] Division of Ser. No. 839,255, Mar. 13, 1986, Pat. No. 4,783,487.

[51] Int. Cl.$^4$ .................. C07C 65/05; C07C 69/86; C07C 69/88; A61K 31/165
[52] U.S. Cl. .................. 514/563; 562/453; 560/39; 560/138; 514/534; 514/535
[58] Field of Search .................. 562/453; 560/39, 138; 514/563, 534, 535

*Primary Examiner*—David B. Springer
*Attorney, Agent, or Firm*—Joseph A. Marlino; Stuart R. Suter; Alan D. Lourie

[57] ABSTRACT

Amide derivatives of non-steroidal anti-inflammatory carboxylic acids which have anti-inflammatory activity in their own right as well as being effective as pro-drugs of the carboxylic acids.

5 Claims, No Drawings

CARBOXYLIC ACID AMIDES, COMPOSITIONS AND MEDICAL USE THEREOF

This is a division of application Ser. No. 839,255 filed Mar. 13, 1986, U.S. Pat. No. 4,783,487

This invention relates to amide derivatives of certain non-steroidal anti-inflammatory carboxylic acids.

One problem associated with some non-steroidal anti-inflammatory carboxylic acids is that they tend to cause gastric irritation. Another problem associated with compounds of this class is that they have a relatively short duration of action. Certain conditions where the patient is suffering from chronic inflammation, require a prolonged level of active drug in order to provide the desired level of pain relief.

We have now discovered a class of amide derivatives of non-steroidal anti-inflammatory carboxylic acids which have anti-inflammatory activity in their own right as well as being effective as pro-drugs of the carboxylic acids. The activity displayed by the compounds is sustained over a relatively long period.

Furthermore amides are relatively stable to metabolism in the gastro-intestinal tract. The compounds are absorbed intact and are split in the liver to produce the free non-steroidal anti-inflammatory acid which is partially absorbed directly from the hepatic blood circulation and partly returned by the bile to the lower gastro-intestinal tract. In this way the local irritant effect on the stomach is significantly reduced.

One mechanism by which non-steroidal anti-inflammatory agents operate is through the inhibition of prostaglandin biosynthesis. One consequence of administering non-steroidal anti-inflammatories is that arachidonic acid, a substrate from which prostaglandins are formed, is diverted into a cascade of enzymatic transformations resulting in the production of leukotrienes.

Leukotrienes cause bronchoconstriction. The administration of non-steroidal anti-inflammatory drugs that block prostaglandin synthesis without blocking leukotriene inhibition results in a condition called respiratory distress syndrome. A further advantage of the compounds of this invention is that they block leukotriene synthesis and hence avoid the development of this syndrome.

According to the present invention there is provided compounds of formula (1):

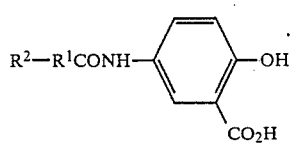

and pharmaceutically acceptable salts and esters thereof where $R^1$ is a single bond or a substituted or unsubstituted alkanediyl group, $R^2$ is a substituted pyrrolyl, thienyl or pyridyl group or a group of formula (2):

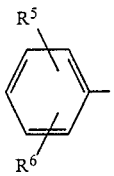

where $R^5$ represents hydrogen or a substituent, $R^6$ represents a substituent or $R^5$ and $R^6$ together represent the residue of a mono- or bicyclic ring;

the group $R^2$ being such that the group of formula (3):

$$R^2-R^1CO \quad (3)$$

represents the residue of a non-steroidal anti-inflammatory carboxylic acid.

The compounds of formula (1) are non-steroidal anti-inflammatory agents and have the anti-inflammatory, analgesic and anti-pyretic properties associated with this class of compounds. They are useful for the treatment of musculo-skeletal disorders especially rheumatoid arthritis, osteoarthritis, periarthritis, tendinitis, tenosynovitis and bursitis.

The group of formula (3):

$$R^2-R^1CO \quad (3)$$

where $R^1$ and $R^2$ are as defined with reference to formula (1) is derived from a non-steroidal anti-inflammatory carboxylic acid of formula (4):

$$R^2-R^1COOH \quad (4)$$

where $R^1$ and $R^2$ are as defined with reference to formula (1).

Throughout this specification, the position of the group $R^2$ is numbered relative to the—$R^1$CONH—moiety.

One class of compounds is that where $R^2$ is a substituted pyridyl group and $R^1$ is a covalent bond. For example, it can be 2-(3-trifluoromethylphenylamino)-3-pyridyl, that is, the group of formula (3) is derived from nifluminic acid.

A further class of compounds within the scope of this invention is where $R^2$ is a substituted pyrrolyl or thienyl group and $R^1$ is a substituted or unsubstituted alkanediyl group. In particular $R^2$ is 1-p-chlorophenyl-2,5-dimethyl-3-pyrrolyl and $R^1$ is methylene, that is, the group of formula (3) is derived from clopirac or $R^2$ is 1-methyl-5-p-toluoyl-2-pyrrolyl and $R^1$ is methylene, that is, the group of formula (3) is derived from tolmetin, or $R^2$ is 5-benzoyl-2-thienyl and $R^1$ is ethane-1,1-diyl, that is, the group of formula (3) is derived from tiaprofenic acid.

A further class of compounds within the scope of this invention is where $R^2$ is a substituted indenyl group. In particular it can be 5-fluoro-3-methyl-1-[p-(methylsulfinyl)benzylidene]-3-indenyl, that is, the group of formula (3) is derived from sulindac.

A further class of compounds within the scope of this invention is where $R^2$ is a substituted indolyl group and $R^1$ is methylene. In particular $R^2$ can be 1-(p-chlorobenzoyl)-5-methoxy-2-methyl-3-indolyl, that is, the group of formula (3) is derived from indomethacin or $R^2$ is 3-(p-chlorobenzoyl)-6-methoxy-2-methyl-1-indolyl, that is, the group of formula (3) is derived from clometacin, or it is 1-cinnamoyl-5-methoxy-2-methyl-3-indolyl, that is, the group of formula (3) is derived from cinmetacin.

A further group of compounds within the scope of this invention is where $R^2$—$R^1CO$ represents a group of formula (5):

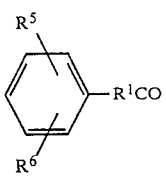

One class of compounds within the scope of this invention is where $R^1$ is a single bond.

A sub-group of compounds within this group is where $R^5$ is hydrogen and $R^6$ is in position 2. Examples of such compounds are where $R^6$ is 2-acetoxy, that is the group of formula (5) is derived from acetylsalicylic acid; or $R^6$ is 2-(3-trifluoromethylphenylamino) that is the group of formula (5) is derived from flufenamic acid; or $R^6$ is 2-(2,6-dichloro-4-methylphenylamino) that is the group of formula (5) is derived from meclofenamic acid; or $R^6$ is 2-(2,3-dimethylphenylamino) that is where the group of formula (5) is derived from mefenamic acid.

A second sub-group of compounds where $R^2$—$R^1CO$ is a group of formula (5) where $R^1$ is a covalent bond is where $R^5$ is a hydroxyl group in position 2, and $R^6$ is a 5-(2,4-difluorophenyl) group that is the group of formula (5) is derived from diflunisal.

A further group of compounds of formula (1) where $R^2$—$R^1CO$ is a group of formula (5) is where $R^1$ is methylene. Within this class $R^5$ can be hydrogen and $R^6$ can be 2-(2,6-dichlorophenylamino) that is the group of formula (5) is derived from dichlofenac, or $R^5$ can be 3-chloro and $R^6$ can be 4-allyloxy that is the group of formula (5) is derived from alclofenac, or $R^5$ and $R^6$ together represent the residue of a 10-methylphenothiazine group that is the group of formula (5) is derived from metiazinic acid.

A further group of compounds within the scope of this invention where $R^2$—$R^1CO$ is a group of formula (5) is where $R^1$ is ethane-1,1-diyl. Within this group of compounds, $R^5$ can be hydrogen and $R^6$ can be 3-phenoxy, that is the group of formula (5) is derived from phenoxyprofen, or $R^6$ is 4-(2-methylpropyl) that is the group of formula (5) is derived from ibuprofen or $R^6$ is 1-oxo-2-isoindolyl that is the ggroup of formula (5) is derived from indoprofen.

A further sub-group within the group of compounds of formula (1) where $R^2$—$R^1CO$ is a group of formula (5) is where $R^1$ is ethane-1,1-diyl and $R^5$ and $R^6$ together represent the residue of a 7-methoxy-10-methylphenothiazine group, that is the group of formula (5) is derived from protizinic acid or $R^5$ and $R^6$ together represent the residue of a 6-methoxynaphthyl group so that the group of formula (5) is derived from naproxen.

Preferably the group of formula (5) is derived from diclofenac or ibuprofen.

Particularly preferred compounds of formula (1) are: N-(1-carboxy-2hydroxy-5-phenyl)-2-[(2,6-dichlorophenyl)amino]acetamide N-(1-carboxy-2-hydroxy-5-phenyl)-2-(4-isobutylphenyl)-propionamide N-(1-carboxy-2-hydroxy-5-phenyl)-d-2-(6-methoxy-2-naphthyl)propionamide, and N-(1-carboxy-2-hydroxy-5-phenyl)-1-(4-chlorobenzoyl)-5-methoxy-2-methyl-1H-indole-3-acetamide.

The phenolic hydroxyl group is acidic and like the carboxyl group can form salts with bases. In addition, the hydroxyl and carboxyl group can also form esters. Reference to pharmaceutically acceptable salts and esters herein means a salt or ester of the hydroxyl or carboxyl group or both.

Examples of salts are alkali-metal salts for example the sodium salt and alkaline-earth metal salts for example the magnesium salt.

Examples of ester groups for the hydroxyl group are acetyl and propionyl esters.

Examples of ester groups for the carboxyl group are $C_{1-4}$alkyl groups especially methyl, ethyl and propyl.

5-Aminosalicylic acid is the active principle in the compound sulphasalazine which has been used in the treatment of Crohn's disease and ulcerative colitis. One of the original therapeutic uses of sulphasalazine was as a disease modifying agent for the treatment of arthritis, that is an agent which can arrest the progress of the disease, and it has been reintroduced for this purpose. Recently it has been found that sulphasalazine is metabolized in vivo to produce 5-aminosalicylic acid and sulphapyridine. In Crohn's disease and ulcerative colitis 5-aminosalicylic acid is responsible for the therapeutic acitivity of sulphasalazine whereas sulphapyridine is responsible for the main side effects. Thus 5-aminosalicylic acid and compounds which give rise to it in vivo may also be particularly useful in the treatment of arthritis.

5-Aminosalicylic acid is relatively unstable and therefore difficult to use as a therapeutic agent in its own right. An advantage of the compounds of this invention is that while the group $R^2$—$R^1CO$ has a stabilising effect on the 5-aminosalicylic acid moiety, the acids $R^2$—$R^1CO_2H$ do not have the undesired side effects associated with sulphasalazine. So the compounds of this class provide in a single molecule two different therapeutic principles free of their most significant disadvantages.

The compounds of formula (1) can be prepared by reacting a non-steroidal anti-inflammatory carboxylic acid of formula (4):

$$R^2—R^1COOH \qquad (4)$$

where $R^1$ and $R^2$ are as defined with reference to formula (1) or an activated esterifying derivative thereof with a compound of formula (6):

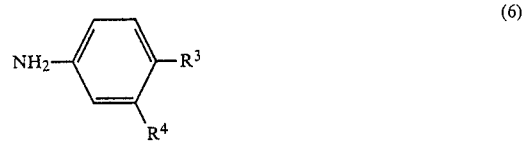

where $R^3$ is hydroxyl or is a protected hydroxyl group and $R^4$ is carboxyl or a protected carboxyl group, where necessary in the presence of an acylation catalyst, thereafter removing any protecting groups from the groups $R^3$ or $R^4$ and optionally converting the hydroxyl and carboxyl groups into a pharmaceutically acceptable salt or ester.

Examples of acylating derivatives of compounds of formula (4) are acid halides and mixed anhydrides.

Examples of acylation catalysts are in particular condensation reagents used in peptide chemistry for example dicyclohexylcarbodiimide and especially 1-ethyl-3-(3-dimethylaminopropyl)carbodiimide.

The use of protecting groups is discussed in J. F. McOmie, Protective Groups in Organic Chemistry, 1973, Plenum Press, IBSN 0-306-30717-0.

Preferably the reaction is carried out in the presence of an organic solvent at moderate temperature using one molar equivalent of the compounds of formulae (4) and (6).

Compounds of formula (1) can be converted into pharmaceutically acceptable salts by standard methods for example reaction with a base and into pharmaceutically acceptable esters by reaction with an esterifying agent.

The starting materials of formulae (4) and (6) are known or can be made by analogy with known methods.

The ability of the compounds of this invention to reduce inflammation can be demonstrated in vivo using the rat's paw carrageenin oedema test as described by Hofrichter et al, Arzn. Forsch. 1969, 19, 2016, and Winter et al, Proc. Soc. Exp. Biol. Med. 111, 544 (1962). The compound of Example 1 can reduce swelling by more than 50% at a dose of 29.2 mg kg$^{-1}$ i.g.

The potential usefulness of the compounds for treating chronic inflammation in arthritic conditions can be assessed using the standard adjuvant arthritis test in the rat. The compound of example 1 was administered at a dose of 0.73 mg/kg daily for 14 days: oedema at the affected right hind paw as well as the secondary reaction on the left hind paw was reduced significantly compared to controls (p 0.05) and the decrease in body weight associated with the arthritic condition was significantly suppressed.

The effect of the compounds on the incidence and severity of indomethacin-induced intestinal ulcers was tested according to the method of Del Soldato, Agents and Actions, 16, 393–396. After administration of indomethacin (16 mg/kg) rats pretreated with the compound of Example 1 (1 50 mg/kg) showed intestinal ulceration in 61% of cases compared with 92% of control rats. Pretreatment with the compound of Example 1 at a dose level of 400 mg/kg totally suppressed ulcer development.

The ability of the compounds of this invention to reduce inflammation can be demonstrated in vitro by measuring their ability to inhibit prostaglandin synthesis in cultured macrophages by the method described by Brune et al, Archives of Pharmacol. 1981, 315, 269. The compound of Example 1 can reduce PGE$_2$ production by over 20% at doses of $3.3 \times 10^{-6}$ molar.

The ability of the compounds of this invention to inhibit leukotriene synthesis can be demonstrated in vitro using the mouse peritoneal macrophage test described by Brune et al, Agents and Actions 1984, 14, 729.

In order to use the compounds of the invention as anti-inflammatory agents, they can be formulated as pharmaceutical compositions in accordance with standard pharmaceutical procedure.

The invention also includes pharmaceutical compositions comprising a compound of formula (1) or a pharmaceutically acceptable salt or an ester thereof and a pharmaceutically acceptable carrier. In addition, the invention includes a method of treating inflammation by administering to a mammal an effective but non-toxic amount of a compound of formula (1) or a pharmaceutically acceptable salt or an ester thereof and a method of treating rheumatoid arthritis or osteoarthritis by administering said compounds.

Compounds of formula (1) can be administered topically or systemically.

Topical formulations for administration to the skin include lotions and creams.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositiions consist of a solution or suspension of the active material in a sterile aqueous carrier or parenterally acceptable oil.

Compounds of formula (1) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet or capsule so that the patient may administer to himself a single dose.

As is common practice, the compositions will usually be accompanied by written or printed directions for use in the medical treatment concerned, in this case as anti-inflammatory agents for the treatment of, for example, rheuamtoid arthritis, osteoarthritis, periarthritis, tendinitis, tenosynovitis and bursitis.

Each dosage unit for oral administration contains preferably from 5 to 200 mg of a compound of formula (1).

The compounds of the invention will normally be administered to a subject for the treatment of rheumatoid arthritis, osteoarthritis, periarthritis, tendinitis, tenosynovitis and bursitis. An adult patient will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (1), the composition being administered 1 to 4 times per day.

The following Examples illustrate the invention.

Example 1

1-Ethyl-3-(3-dimethylaminopropyl)carbodiimide hydrochloride (1.91 g) was added to a chilled (0°) suspension of 5-aminosalicylic acid (1.6 g), diclofenac (2.9 g) and triethylamine (1.0 g) in dichloromethane (200 ml) with stirring.

The mixture was stirred for 3 hrs. The reaction mixture was washed with hydrochloric acid (0.1N) to remove the triethylamine and unreacted 5-aminosalicylic acid. The organic layer was isolated, dried and the solvent removed. The residue was recrystallised from methanol/water to yield N-(1-carboxy-2-hydroxy-5-phenyl)-2-[(2,6-dichlorophenyl)amino] acetamide (1.4 g, 30%) m.p. 260° as a white powder. This compound was soluble in ethanol, acetone and aqueous alkali and had $\lambda_{max}$ (ethanol) 254 nm.

Example 2

Substituting ibuprofen (5.2 g) for diclofenac in the process of Example 1 and using 5-aminosalicylic acid (3.06 g), triethylamine (2.09 g) and 1-ethyl-3-(3-dimethylaminopropyl)carbodiimide hydrochloride (3.95 g) in methylene chloride (200 ml) yielded N-(1-carboxy-2-hydroxy-5-phenyl)-2-(4-isobutylphenyl)propionamide (1.5 g, 20%) m.p. 238° C.; M+ (m.s.) 341.

Example 3

Substituting naproxen (7.07 g) for diclofenac in the process of Example 1 and using 5-aminosalicylic acid (4.72 g), triethylamine (3.15 g) and 1-ethyl-3-(3-dimethylaminopropyl)carbodiimide hydrochloride (5.88 g) in methylene chloride (200 ml) yielded N-(1-carboxy-2-hydroxy-5-phenyl)-d-2-(6-methoxy-2-naphthyl) propionamide (2.4 g; 20%) m.p. 220° C.; M+ (m.s.) 365.

Example 4

Substituting indomethacin (3.52 g) for diclofenac in the process of Example 1 and using 5-aminosalicylic acid (1.66 g), triethylamine (1.13 g) and 1-ethyl-3-(3-dimethylaminopropyl)carbodiimide hydrochloride (1.94 g) in methylene chloride (100 ml) yielded N-(1-carboxy-2-hydroxy-5-phenyl)-1-(4-chlorobenzoyl)-5-methoxy-2-methyl-1H-indole-3-acetamide, (1.1 g, 20%) m.p. 256 ° C.; M+ (m.s.) 492.

Example 5

A tablet for oral administration is prepared by combining

|  | mg/tablet |
|---|---|
| N—(1-carboxy-2-hydroxy-5-phenyl)-2-[(2,6-dichlorophenyl)amino] acetamide | 100 |
| Mannitol | 153 |
| Starch | 33 |
| Polyvinyl pyrollidone | 12 |
| Microcrystalline cellulose | 30 |
| Magnesium Stearate | 2 | into a tablet using standard pharmaceutical procedures.

What is claimed is:

1. The compound N-(1-carboxy-2-hydroxy-5-phenyl)-2-[(2,6-dichlorophenyl)amino]acetamide and pharmaceutically acceptable salts and esters thereof.

2. A pharmaceutical composition comprising a non-toxic but therapeutically effective amount of the compound of claim 1 and a pharmaceutically acceptable carrier.

3. A method of treating musculo-skeletal disorders in a mammal, which method comprises administering to said mammal a therapeutically effective but non-toxic amount of the compound of claim 1.

4. The method of claim 3 wherein the musculo-skeletal disorder is rheumatoid arthritis or osteoarthritis.

5. A method of treating inflammation in a mammal, which method comprises administering to said mammal a therapeutically effective but non-toxic amount of the compound of claim 1.

* * * * *